(12) United States Patent
Jaremo et al.

(10) Patent No.: US 6,488,624 B1
(45) Date of Patent: Dec. 3, 2002

(54) DEVICE FOR MEASURING THE ELASTICITY OF RED BLOOD CORPUSCLES (ERYTHROCYTES)

(75) Inventors: Petter Jaremo, Norrkoping (SE); Per Hvass, Tullinge (SE)

(73) Assignee: Gematron Medical AB, Skarholmen (SE)

(*) Notice: Subject to any disclaimer, the term of this patent is extended or adjusted under 35 U.S.C. 154(b) by 0 days.

(21) Appl. No.: 09/701,568

(22) PCT Filed: Jun. 9, 1999

(86) PCT No.: PCT/SE99/01004

§ 371 (c)(1),
(2), (4) Date: Jan. 31, 2001

(87) PCT Pub. No.: WO99/67635

PCT Pub. Date: Dec. 29, 1999

(30) Foreign Application Priority Data

Jun. 20, 1998 (SE) ............................................. 9802217

(51) Int. Cl.⁷ ........................ G01N 33/487; G01N 33/49
(52) U.S. Cl. ..................................................... 600/368
(58) Field of Search .................................. 600/368, 369, 600/370, 308, 300; 73/64.41; 422/73; 222/103; 604/317, 318, 403, 404, 409

(56) References Cited

U.S. PATENT DOCUMENTS

| | | | |
|---|---|---|---|
| 4,317,363 A | * | 3/1982 | Shen .......................... 73/64.41 |
| 4,348,890 A | * | 9/1982 | Hanss ......................... 73/61.64 |
| 4,521,729 A | * | 6/1985 | Kiesewetter et al. ........ 324/71.1 |
| 5,205,159 A | * | 4/1993 | Carr, Jr. ....................... 422/73 |
| 5,293,772 A | | 3/1994 | Carr |

FOREIGN PATENT DOCUMENTS

DE WO 9314401 * 6/2000 ............ G01N/3/08

* cited by examiner

Primary Examiner—Kevin Shaver
Assistant Examiner—Navin Natnithithadha
(74) Attorney, Agent, or Firm—Dennison, Schultz & Dougherty

(57) ABSTRACT

When injecting red blood corpuscles it is important to know their elasticity since they can alter from an elastic to a substantially rigid state. The present invention allows it to be ascertained whether the elasticity fulfills the requirements stipulated.

3 Claims, 1 Drawing Sheet

DEVICE FOR MEASURING THE ELASTICITY OF RED BLOOD CORPUSCLES (ERYTHROCYTES)

BACKGROUND OF THE INVENTION

Figure 1:
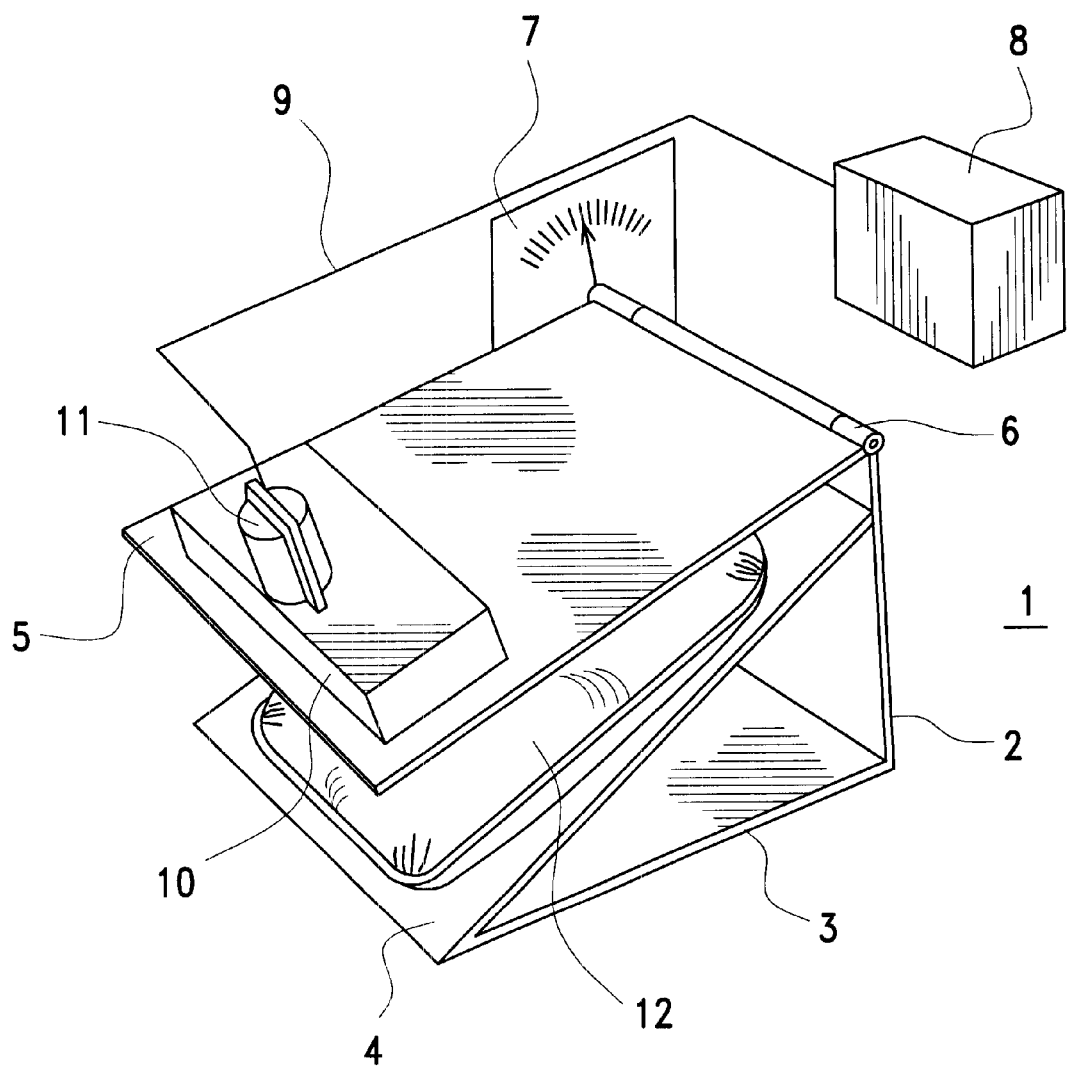

The present invention relates to a device for measuring the elasticity of red blood corpuscles (Erythrocytes). Red blood corpuscles are stored under sterile conditions in plastic bags together with nutrient such as SAG-M solution. In the case at certain conditions of disease red blood corpuscles only have to be injected, and to enable injection the quality of the red blood corpuscles must be known. Hitherto no means has been available for determining the elasticity of the red blood corpuscles and it has just been assumed that after a certain period of storage the red blood corpuscles cannot be used for injection purposes and must therefore be rejected. It is normally assumed that red blood corpuscles can be stored for about 60 days at a storage temperature of between 4 end 6° C. Initially the red blood corpuscles are elastic and mouldable but become gradually stiffer with time, which means that when the elasticity has fallen to a certain level the rod blood corpuscles can no longer be injected since this would cause problems in conjunction with injection.

SUMMARY OF THE INVENTION

The object of the present invention is to provide a device with the aid of which it is possible to determine the elasticity of the red blood corpuscles so that the lowest tolerable elasticity can immediately be determined. For this purpose two surfaces are used which can be moved towards and away from each other, one of the surfaces being stationary while the other can be moved towards or away from the lower surface. A package, e.g. a plastic bag, containing red blood corpuscles and nutrient, the contents being sterile, is placed between the two surfaces. The movable surface is subjected to a pressure applied thereon so that the surface is continuously under a predetermined pressure. The weighted surface is subjected to extra pressure pulses with intervals between, whereupon the time is measured for the cell to resume the shape it had prior to a pressure pulse. This measuring procedure can be repeated and transferred to a computer, with the aid of which information is available as to whether the contents of the bag being tested is suitable for injecting or not. It has proved suitable for the two surfaces to be in the shape of a rectangular plates, one plate being movable and the other stationary, the ends of the plates being pivotably joined together by means of a suitable hinge construction. The point of pivot is suitably arranged at a distance from a support surface, whereas the other and of the lower plate abuts the support surface. A suitable angle for the lower plate in relation to the support surface is in the order of 45°. With this arrangement also the bag is placed between the plates and the upper plate is subjected to pressure. In this case no distance can be measured between the two plates and instead the angle prevailing when the red blood corpuscles have been compressed as far as possible is measured. After which the time is measured from when a pulse ceases to when the red blood corpuscles resume their normal shape. The frequency of the pressure and variations in the angle are transferred to a control station which records the necessary data to be able to reach an assessment of whether the red blood corpuscles in the blood bag are injectable or not.

DETAILED DESCRIPTION OF THE INVENTION

The present invention will be described in more detail with reference to the accompanying drawing showing one embodiment of the invention.

The drawing shows a test apparatus 1. The apparatus consists of a side wall 2 and a bottom plate 3, the bottom plate being designed to be placed on a table. A stationary contact plate is arranged between the side wall and the bottom plate. Above the plate 4 is a movable pressure plate 5, movable at the upper end of the side wall 2 with the aid of a suitable hinge construction 6. In the present case the hinge construction is spaced from the upper end of the lower plate. It should, however, be obvious that the hinge 6 can equally well be arranged at the upper end of the plate 4. A suitable angle for the plate 4 in relation to the bottom plate 3 is in the order of 45°. Other suitable angles are of course possible. The movement of the plate 5 is registered by an angle indicator 7. The values are transferred to a control and processing means 8. The processing means 8 is connected by a wire 9 to an electromagnetic impulse emitter 11 arranged on a weight 10 placed on the movable pressure plate 5. A bag containing red blood corpuscles and nutrient is placed between the plates 4 and 5. The contents of the bag is sterile. The impulse emitter 11 may operate continuously at a certain frequency, or it may emit pulses on desired occasions. All this is achieved by means of the control and processing means 8, which also registers the angle between the two plates 4 and 5. When the plastic bag 12 is compressed, the time is measured from pressure to absence of pressure and represents the time the rod blood corpuscles need to resume their naturally elastic original shape.

The advantage of having a stationary contact plate forming an angle with the bottom plate 3 is that all the red blood corpuscles in the bag 12 are then situated as far down in the bag as possible, whereas the nutrient becomes separated as a phase above the red blood corpuscles.

The invention provides a device that ensures that the control and processing means 8 advises whether the rod blood corpuscles are in a form suitable for blood transfusion. A security actor has thus been added.

What is claimed is:

1. A device for measuring the elasticity of red blood corpuscles (Erythrocytes), wherein a quantity of blood corpuscles is stored in a package (12) of elastomeric material, preferably of plastic in the form of a bag, characterized by an upper surface (5) and a lower surface (4) opposite to each other that can be caused to approach each other under pressure and can be moved apart from each other, between which said package (12) is placed, and by members (10 and 11) generating pressure, and by an arrangement (7) registering the relative movement possible between the two surfaces (4 and 5).

2. A device as claimed in claim 1, characterized in that one end of each of the two surfaces (4 and 5) is secured to the other about a transverse shaft (6) so that the surfaces (4 and 5) can be pivoted in relation to each other.

3. A device as claimed in claim 2, characterized in that the lower surface (4) is inclined in relation to a support surface (3), the end about which pivoting occurs being located at a distance from the support surface (3).

* * * * *